United States Patent [19]
Sutoris et al.

[11] Patent Number: 6,143,205
[45] Date of Patent: Nov. 7, 2000

[54] MIXTURES CONTAINING MONOMERS AND STABILIZERS

[75] Inventors: Heinz Friedrich Sutoris, Frankenthal; Alexander Aumüller, Neustadt; Hermann Uhr, Frankenthal, all of Germany

[73] Assignee: BASF Aktiengesellschaft, Ludwigshafen, Germany

[21] Appl. No.: 09/117,178

[22] PCT Filed: May 28, 1997

[86] PCT No.: PCT/EP97/02758

§ 371 Date: Aug. 3, 1998

§ 102(e) Date: Aug. 3, 1998

[87] PCT Pub. No.: WO97/46504

PCT Pub. Date: Dec. 11, 1997

[30] Foreign Application Priority Data

Jun. 5, 1996 [DE] Germany .......................... 196 22 498
Aug. 27, 1996 [DE] Germany .......................... 196 34 470

[51] Int. Cl.[7] .......................... C09K 15/16; C09K 15/22; C09K 15/08; C07C 7/20; C10L 7/20
[52] U.S. Cl. .......................... 252/405; 252/403; 252/404; 252/182.29; 252/183.12; 585/5; 585/3; 585/4
[58] Field of Search .................. 585/5, 3, 4; 252/182.29, 252/183.12, 403, 404, 405

[56] References Cited

U.S. PATENT DOCUMENTS

| | | |
|---|---|---|
| 3,733,326 | 5/1973 | Murayama et al. . |
| 3,988,212 | 10/1976 | Watson . |
| 4,086,147 | 4/1978 | Watson . |
| 4,105,506 | 8/1978 | Watson . |
| 4,132,602 | 1/1979 | Watson . |
| 4,132,603 | 1/1979 | Watson . |
| 4,252,615 | 2/1981 | Watson . |
| 4,341,600 | 7/1982 | Watson . |
| 4,466,904 | 8/1984 | Watson et al. . |
| 4,468,343 | 8/1984 | Butler et al. . |
| 4,654,451 | 3/1987 | Miller et al. ................................ 585/5 |
| 4,967,027 | 10/1990 | Takahashi et al. .......................... 585/5 |
| 5,254,760 | 10/1993 | Winter et al. ................................ 585/5 |

FOREIGN PATENT DOCUMENTS

| | | |
|---|---|---|
| 2211902 | 9/1996 | Canada . |
| 0 240 297 | 10/1987 | European Pat. Off. . |
| 195 10 184 | 9/1996 | Germany . |
| 1-165534 | 6/1989 | Japan . |
| 1027150 | 7/1983 | Russian Federation . |
| 1139722 | 2/1985 | Russian Federation . |
| 1558888 | 4/1990 | Russian Federation . |

*Primary Examiner*—Jill Warden
*Assistant Examiner*—Monique T. Cole
*Attorney, Agent, or Firm*—Oblon, Spivak, McClelland, Maier & Neustadt, P.C.

[57] ABSTRACT

Mixtures contain
(A) vinyl-containing monomers, and
(B) an effective amount of a mixture inhibiting the premature polymerization of the vinyl-containing monomers during the purification or distillation and containing
  (i) from 0.05 to 4.5% by weight, based on the total mixture (B), of at least one N-oxyl compound of a secondary amine which carries no hydrogen atoms on the α-carbon atoms and
  (ii) from 99.95 to 95.5% by weight, based on the total mixture (B), of at least one nitro compound,
and a mixture (B) is used for inhibiting the premature polymerization of monomers.

11 Claims, No Drawings

MIXTURES CONTAINING MONOMERS AND STABILIZERS

The present invention relates to mixtures which, in addition to vinyl-containing monomers for preventing their premature polymerization during purification or distillation, also contain at least one nitroxyl and at least one nitro compound, a process for purifying or distilling such monomers without their premature polymerization taking place, and the use of mixtures which contain nitroxyl and nitro compounds for inhibiting the premature polymerization of vinyl-containing monomers.

It is known that many unsaturated compounds tend to polymerize, as a rule by free radical polymerization, when the temperatures increase. For example, vinylaromatic compounds, such as styrene or α-methylstyrene, must be stabilized with suitable compounds in order to prevent premature polymerization during distillative purification of the crude products obtained on a large industrial scale. Usually, these stabilizers or polymerization inhibitors are added before the purification step to the crude products to be distilled. In spite of this measure, considerable amounts of polymers are still obtained. In individual cases, especially when operational faults occur, complete polymerization of the monomers or monomer mixtures present may occur during purification or distillation. This results in high costs owing to the very complex purification and the loss of production.

USSR patents 1,027,150, 1,558,888 and 1,139,722 describe the stabilization of styrene by the use of nitroxyl or bisnitroxyl compounds.

Japanese publication Hei 1-165 534 discloses I-piperidyloxy derivatives as polymerization inhibitors for styrene. U.S. Pat. No. 35 3,733,326 describes the inhibition of the polymerization of vinyl monomers by using free radical precursor compounds.

Nitro compounds, such as 2-nitro-p-cresol or 2,6-dinitro-p-cresol, are mentioned as polymerization inhibitors in U.S. Pat., No. 4,086,147, 4,105,506 and 4,252,615. U.S. Pat. No. 4,132,602 and 4,132,603 disclose the use of halogenated nitroaromatic compounds for inhibiting the polymerization of vinylaromatics during their distillative working-up.

However, all the stated nitro compounds have only a small stabilizing effect and therefore have to be used in relatively high concentrations. If the relatively high toxicity of these nitrocompounds is also taken into account, their use constitutes a considerable potential danger for the operating personnel and the environment.

The use of inhibitors based on N-nitrosodiphenylamine in combination with dinitrocresol derivatives in the distillation of vinylaromatics under reduced pressure is described in U.S. Pat. Nos. 3,988,212 and 4,341,600. When oxygen is present, polymerization of vinylaromatic compounds on heating can be prevented, according to U.S. Pat. Nos. 4,466,904 and 4,468,343, by using an initiator based on phenothiazine, 4-tert-butylcatechol, 2,6-dinitro-o-cresol or 2,6-dinitro-p-cresol with either phenyldiamine or 4-tert-butylcatechol. According to EP 240 297, polymerization of vinylaromatics on heating can be suppressed by using hydroxylamine derivatives and dinitrophenol. However, a disadvantage of these inhibitor systems is the strong dependence of their efficiency on the oxygen content, i.e. these additives are likely to have different inhibiting effects under the conditions of the purification or distillation, in accordance with the nonuniform distribution of the residual oxygen in the corresponding unit. However, this makes the controlled use more difficult.

U.S. Pat. No. 5,254,760 describes mixtures of nitroxyl and nitro compounds for stabilizing vinylaromatic compounds during purification or distillation. The nitroxyl and nitro compounds are used in amounts of from 5 to 95% by weight and from 95 to 5% by weight, based on the total amount of the mixture. Since nitroxyl compounds are as a rule very expensive, this stabilizing additive, which must be added continuously in a certain amount to the crude product before working-up, constitutes a cost factor which is not negligible.

Furthermore, there is the danger that, when polymerization inhibitors having relatively high contents of nitroxyl compound(s) are used, some of these will be entrained into the pure product and will lead there to inhibition of possibly desirable polymerization.

A further disadvantage of these mixtures is their relatively low efficiency with regard to delaying the polymerization of monomers. If the feed of the inhibitor/crude monomer mixture into the distillation apparatus is interrupted, for example as a result of an operational fault, not only is there a lack of cooling of the column bottom caused by their continuous introduction but in addition, owing to inadequate stabilization, there is an exothermic polymerization with evolution of heat and an associated increase in temperature, which in turn accelerates the polymerization. In extreme cases, extensive polymer formation over a prolonged period may thus render a corresponding purification or distillation unit useless.

Long retardation of the polymerization is therefore an important aspect for the operational use of appropriate inhibitors.

It is an object of the present invention to provide mixtures of vinyl-containing monomers which are effective for a sufficiently long time and are economically stabilized to prevent premature polymerization during the purification or distillation and result in a very small amount of troublesome inhibitor residues in the pure product.

We have found that this object is, achieved and that, surprisingly, all these criteria are fulfilled by mixtures which contain (A) vinyl-containing monomers,
(B) an effective amount of a mixture inhibiting the premature polymerization of the vinyl-containing monomers during their purification or distillation and containing,
  (i) from 0.05 to 4.5% by weight, based on the total mixture (B), of at least one N-oxyl compound of a secondary amine which carries no hydrogen atoms on the α-carbon atoms and
  (ii) from 99.95 to 95.50% by weight, based on the total mixture (B), of at least one nitro compound.

Preferred mixtures are those which contain from 0.1 to 4.0% by weight of the component (i) and from 99.9 to 96% by weight of the component (ii), based in each case on the total mixture (B).

Preferred vinyl-containing monomers (A) are those of the formula (Ia)

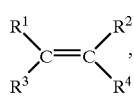

(Ia)

where:
$R^1$, $R^2$, $R^3$ and $R^4$, independently of one another, are each hydrogen, $C_1$–$C_6$-alkyl, $C_2$–$C_6$-alkenyl, unsubstituted or substituted aromatic or heteroaromatic radicals or halogen, with the proviso that not more than two of these radicals are simultaneously unsubstituted or substituted aromatic or heteroaromatic radicals.

The $C_1-C_6$-alkyl radicals include the linear alkyl chains of methyl through ethyl to hexyl as well as the corresponding branched radicals. Furthermore, suitable $C_2-C_6$-alkenyl radicals are ethenyl, propenyl, etc. up to hexenyl and the groups which are branched in the saturated moiety. Examples of both unsubstituted and substituted aromatic or heteroaromatic groups are phenyl, pyridyl, alkylphenyl or alkylpyridyl, such as methylphenyl, methylpyridyl, ethylphenyl or ethylpyridyl, alkenylphenyl or alkenylpyridyl, such as vinylphenyl or vinylpyridyl, carboxyphenyl or carboxypyridyl, formylphenyl or formylpyridyl, sulfophenyl or sulfopyridyl, hydroxyphenyl or hydroxypyridyl, aminophenyl or aminopyridyl, nitrophenyl or nitropyridyl, as well as naphthyl or napthyl substituted by alkyl, alkenyl, carboxyl, formyl, sulfo, hydroxyl, amino or nitro. The halogen radical usually used is fluorine or chlorine, and occasionally also bromine.

If, for example, compounds having in each case an aromatic or heteroaromatic radical on the one hand and a $C_1-C_6$-alkyl radical on the other hand are considered, and if the remaining two radicals from $R^1$, $R^2$, $R^3$ and $R^4$ are each hydrogen, examples of monomers to be added are α-methylstyrene (2-phenyl-prop-1-ene), the two β-methylstyrene isomers (cis- and trans-1-phenyl-prop-1-ene), α-ethylstyrene (2-phenylbut-1-ene), the two β-ethylstyrene isomers (cis- and trans-1-phenylbut-1-ene) up to a-hexylstyrene (2-phenyloct-1-ene) and the two β-hexylstyrene isomers (cis- and trans-1-phenyloct-1-ene).

Similarly, when pyridyl is used instead of the phenyl radical, the compounds 2-pyridyl-prop-1-ene, cis- and trans-1-pyridyl-prop-1-ene, 2-pyridylbut-1-ene, cis- and trans-1-pyridylbut-1-ene up to 2-phenyloct-1-ene and the two isomers cis-1-pyridyl-oct-1-ene and trans-1-pyridyloct-1-ene are obtained. Also included here are of course the isomers which differ in the position of the pyridine-N-atom relative to the bond linking the vinyl to the pyridyl group. If the phenyl or pyridyl radical is substituted by the abovementioned groups, compounds such as α-methylstyrenesulfonic acid (2-sulfophenylprop-1-ene), α-methylnitrostyrene (2-nitrophenylprop-1-ene), αethyl-styrenesulfonic acid (2-sulfophenylbut-1-ene), α-ethyl-nitrostyrene (2-nitrophenylbut-1-ene), the analogous pyridyl monomers or the cis/trans-isomers of the corresponding β-substituted compounds are obtained. Here too, the isomers which arise from the position of the substituent on the benzene ring relative to the phenyl-vinyl bond or, in the case of the substituted pyridene radical, from the relative position of the pyridine N-atom, substituent and pyridyl-vinyl bond to each other are of course included.

By choosing an aromatic or heteroaromatic radical on the one hand and a $C_2-C_6$-alkenyl group on the other hand, and if the two remaining radicals are once again hydrogen, substituted butadienes are also among the monomers which can be obtained. It is possible to use, for example, the compounds 1- or 2-phenylbutadiene, 1- or 2-pyridylbutadiene with the corresponding cis/transisomers on the one hand and, in the case of the pyridyl radical, once again the positional isomers arising from the relative position of the N atom to the pyridyl-vinyl bond. Here too, various substituents mentioned further above may occur on the aromatic or heteroaro-matic system.

According to the invention, aromatically or heteroaromatically substituted ethylenes, such as styrene, vinylpyridine, divinylbenzene, nitrostyrene, styrolsulfonic acids, vinyltoluene and, if desired, isomers thereof may also be used.

According to the formula (Ia), three of the radicals $R^1$, $R^2$, $R^3$, $R^4$ are hydrogen and only one is an aromatic or heteroaromatic unsubstituted or substituted group in these monosubstituted ethylenes, i.e. in the order of phenyl, pyridyl, vinylphenyl, nitrophenyl, sulfophenyl and methylphenyl. If desired, disubstituted ethylenes in which two or four radicals $R^1$, $R^2$, $R^3$, $R^4$ are hydrogen and the remaining radicals are aromatic or heteroaromatic groups may also be used. Usually, these are symmetrically substituted stilbenes such as 4,4'-diaminostilbene, 4,4'-dinitrostilbene, 4,4'-dinitrostilbene-2,2'-disulfonic acid, 4,4'-diaminostilbene-2,2'- disulfonic acid (flavonic acid) or their cis- or trans-isomers. It is of course also possible to use those isomers which differ from one another with respect to the position of the substituent or of the substituents in the aromatic of heteroaromatic system relative to the vinyl group. According to the formula (I), in these stilbenes two of the radicals $R^1$, $R^2$, $R^3$, $R^4$ are hydrogen and the remaining radicals are nonvicinal radicals, which in this case are also identical, in the order aminophenyl, nitrophenyl, nitrosulfophenyl and aminosulfophenyl.

Halogen-containing monomers, such as vinyl chloride, vinylidene chloride, vinyl fluoride, vinyl bromide and chloroprene (2-chloro-1,3-butadiene) may also be used in the claimed mixtures.

It is of course possible to use the vinyl-containing monomers not only as a mixture with their isomers but also as a mixture with one another, as obtained in the crude product, for example in their preparation.

Further preferred vinyl-containing monomers (A) are those of the formula (Ib)

  (Ib), where

Q is oxygen or $—NZ^2—$,

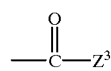

$Z^2$ is hydrogen or $C_1-C_4$-alkyl or, together with $Z^3$, is a saturated or unsaturated $C_3$-, $C_4$- or $C_5$-alkylene bridge in which one or two $CH_2$ groups may be replaced by NH, $N(C_1-C_4$-alkyl), $N(C_6-C_{10}$-aryl) or oxygen and one or two CH groups may be replaced by N and $Z^3$ is hydrogen, $C_1-C_4$-alkyl or a radical which, together with $Z^2$, is a saturated or unsaturated $C_3$-, $C_4$- or $C_5$-alkylene bridge in which one or two $CH_2$ groups may be replaced by NH, $N(C_1-C_4$-alkyl), $N(C_6-C_{10}$-aryl) or oxygen and one or two CH groups may be replaced by N.

The monomers (A) of the formula (Ib) which are contained in the novel mixtures may contain oxygen as Q. Among these monomers, the vinyl ethers in which $Z^1$ is $C_1-C_4$-alkyl, i.e. methyl, ethyl, n-propyl, isopropyl, n-butyl, isobutyl, sec-butyl or tert-butyl, are particularly suitable as a component of the novel monomer compositions.

If Q is $—NZ^2—$, $Z^1$ is preferably $—CO—Z^3$.

Other suitable radicals $Z^3$ in addition to hydrogen and the stated $C_1-C_4$-alkyl groups are those radicals, which, together with $—NZ^2—$, form a saturated or unsaturated 5- to 7-membered ring. Examples of such ring systems are:

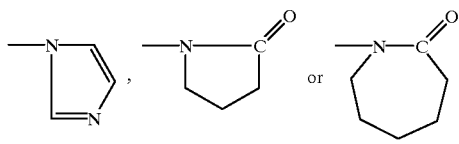
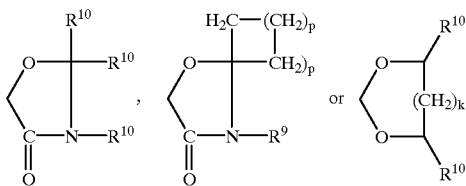

in particular the N-pyrrolidinonyl and the N-caprolactamyl radicals.

Preferred monomers in the novel compositions are N-vinylformamide, N-vinyl-2-pyrrolidone, N-vinyl-ε-caprolactam and the above-mentioned $C_1$–$C_4$-alkyl vinyl ethers.

N-vinylformamide is particularly preferred among these monomers.

Preferred N-oxyl compounds in the novel monomer compositions are those of the general formula (II)

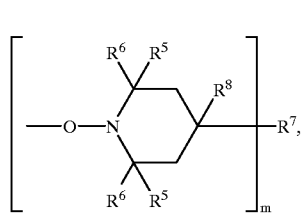

(II)

where $R^5$ and $R^6$, independently of one another, are each $C_1$–$C_4$-alkyl, or phenyl or, together with the carbon atom to which they are bonded, are a 5- or 6-membered saturated hydrocarbon ring, $R^7$ is hydrogen, hydroxyl, amino or an m-valent organic radical bonded via oxygen or nitrogen or, together with $R^8$, is oxygen or a ring structure defined under $R^8$, $R^8$ is hydrogen, $C_1$–$C_{12}$-alkyl or, together with $R^7$, is oxygen or, together with $R^7$ and the carbon atom to which they are bonded, forms the following ring structures where, when $R^7$ together with $R^8$ forms a common radical, m is 1, $R^9$ is hydrogen, $C_1$–$C_{12}$-alkyl or —$(CH_2)_z$—$COOR^{10}$, R10 are identical or different $C_1$–$C_{18}$-alkyl radicals, k is 0 or 1, z and p, independently of one another, are each from 1 to 12 and m is from 1 to 100.

$R^5$ and $R^6$ may be $C_1$–$C_4$-alkyl, such as methyl, ethyl, n-propyl, isopropyl, n-butyl, isobutyl, sec-butyl or tert-butyl or together may form a tetra- or pentamethylene group. $R^5$ and $R^6$ are each preferably methyl.

Examples of suitable radicals $R^8$ are hydrogen, the abovementioned $C_1$–$C_4$-alkyl groups and pentyl, sec-pentyl, tert-pentyl, neopentyl, hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, undecyl, isoundecyl, dodecyl and isododecyl, (the names isooctyl, isononyl and isodecyl are trivial names and originate from the carbonyl compounds obtained by the oxo synthesis; cf. Ullmann's Encyclopedia of Industrial Chemistry, 5th Edition, Vol. A1, Pages 290–293, and Vol. A10, Pages 284 and 285).

p is preferably from 6 to 12, particularly preferably 9.

z is preferably from 1 to 4, particularly preferably 2.

Examples of suitable radicals $R^9$ in addition to hydrogen are the abovementioned $C_1$–$C_{12}$-alkyl groups. $R^9$ is preferably hydrogen, $C_1$–$C_4$-alkyl or $(CH_2)_z$—$COO(C_1$–$C_6$-alkyl), particularly preferably —$CH_2$—$CH_2$—$COO(CH_2)_{11}$—$CH_3$ and —$CH_2$—$CH_2$—$COO(CH_2)_{13}$—$CH_3$.

$R^{10}$ may be, for example, one of the abovementioned $C_1$–$C_{12}$-alkyl groups or tridecyl, isotridecyl, tetradecyl, pentadecyl, hexadecyl, heptadecyl or octadecyl. Dodecyl and hexadecyl are preferred.

Preferred monovalent organic radicals $R^7$ bonded via oxygen are hydroxyl and $(C_1$–$C_4)$-alkoxy groups, for example methoxy, ethoxy, propoxy or tert-butoxy.

Preferred m-valent radicals $R^7$ are, for example, the following radicals

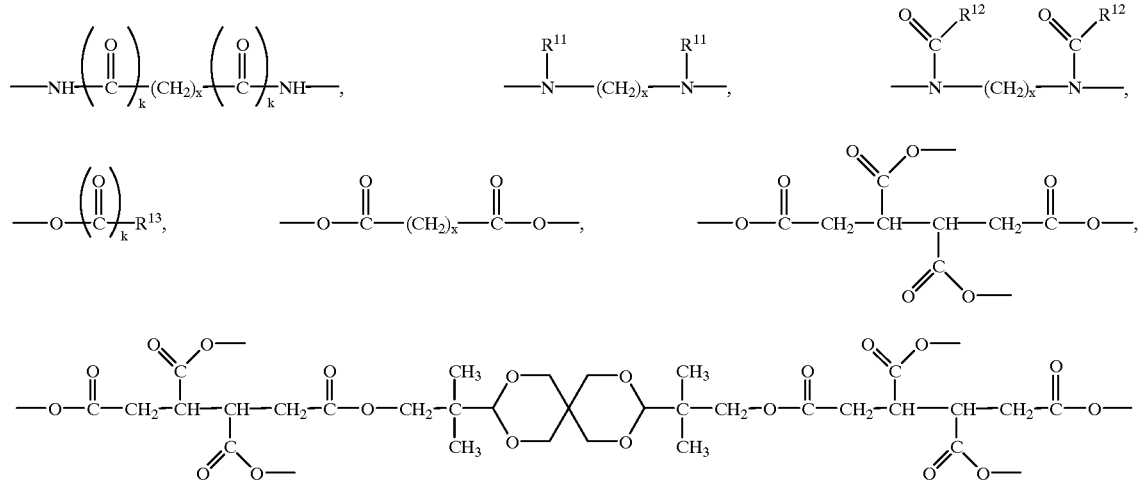

-continued

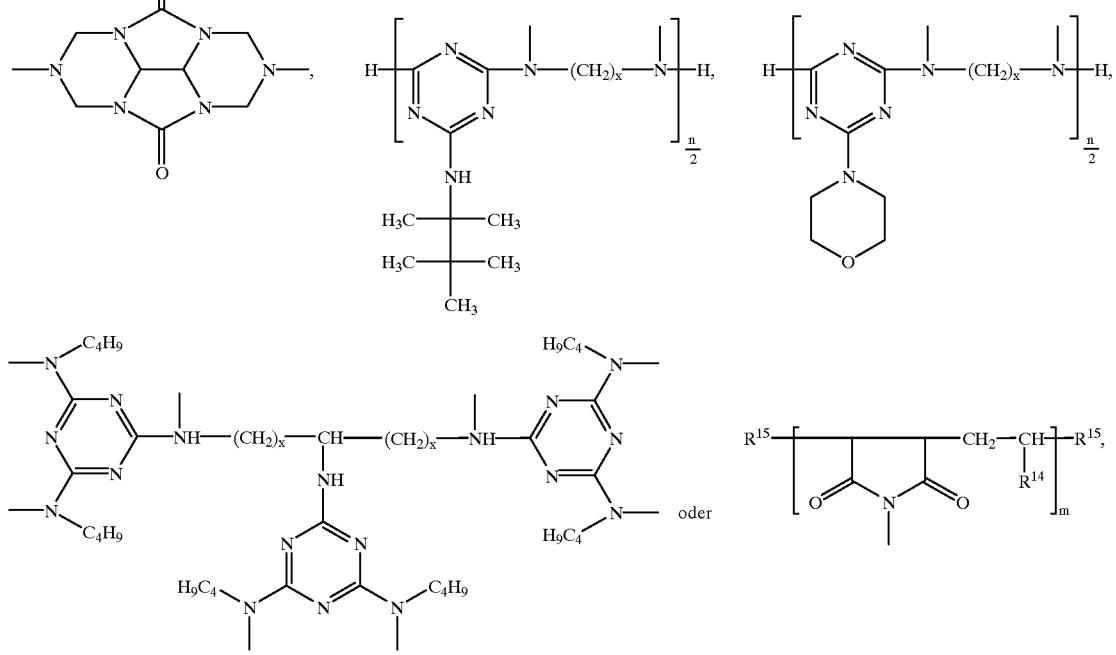

where
R¹¹ is $C_1$–$C_{12}$-alkyl or —$(CH_2)_z$—$COOR^{10}$,
R¹² is hydrogen or $C_1$–$C_{18}$-alkyl,
R¹³ is $C_1$–$C_{18}$-alkyl, vinyl or isopropenyl,
R¹⁴ is $C_8$–$C_{22}$-alkyl,
R¹⁵ is hydrogen or an organic radical as usually formed in the free radical polymerization of the starting monomers,
k is 0 or 1,
x is from 1 to 12 and
n is an even number m.

If R⁷ is one of these radicals, R⁸ is preferably hydrogen. m may be from 1 to 100. m is preferably 1,2,3,4 or a number from 10 to 50, mixtures generally being used especially in the case of the oligomeric or polymeric radicals R⁷.

Suitable radicals R¹¹ are the same radicals as stated for R⁹. R¹¹ is preferably $C_1$–$C_4$-alkyl.

Suitable radicals R¹² in addition to hydrogen are the same radicals as have been stated for R¹⁰. R¹² is preferably hydrogen.

Suitable radicals R¹³ are vinyl, isopropenyl and $C_{15}$–$C_{17}$-alkyl.

Examples of suitable radicals R¹⁴ are the abovementioned $C_8$–$C_{18}$-alkyl radicals and nonadecyl, eicosyl, uneicosyl and doeicosyl. Mixtures of different radicals R¹⁴, which differ in the length of the carbon chain are preferred.

R¹⁵ is hydrogen or an organic radical as formed in the free radical polymerization of the starting monomers, for example a radical which is formed from the polymerization initiator or from a radical occurring as an intermediate, or another such radical as is familiar to a person skilled in the art.

Preferred nitroxyl compounds as component (i) of the novel monomer compositions are also the following:
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethylpiperidin-4-yl acetate,
1-oxyl-2,2,6,6-tetramethylpiperidin-4-yl 2-ethylhexanoate,
1-oxyl-2,2,6,6-tetramethylpiperidin-4-yl stearate,
1-oxyl-2,2,6,6-tetramethylpiperidin-4-yl benzoate,
1-oxyl-2,2,6,6-tetramethylpiperidin-4-yl (4-tert-butyl) benzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl) adipinamide,
N-(1-oxyl-2,2,6,6-tetramethylpiperidin-4-yl)caprolactam,
N-(1-oxyl-2,2,6,6-tetramethylpiperidin-4-yl) dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one),
N,N'-bis(1-oxyl-2,2,6,6-tetramethylpiperidin-4-yl)-N,N'-bis-formyl-1,6-diaminohexane and
tris-(2,2,6,6-tetramethyl-1-oxylpiperidin-4-yl) phosphite.

The nitroxyl compounds described can be prepared from the corresponding piperidine compounds by oxidation, for example with hydrogen peroxide. Details of this oxidation are stated, for example, in the prior German patent application 195 101 84.7. The secondary amines which carry no hydrogen atoms on the α-carbon atoms, such as piperidine compounds, and their preparation are generally known. Since the oxidation reactions do not always go to completion, the piperidine compounds serving as starting compound and partially oxidized intermediates may also be present in the novel monomer compositions.

Monomer mixtures contain, as component (ii), at least one aromatic nitro compound of the formula (III)

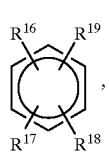

(III)

where $R^{16}$, $R^{17}$, $R^{18}$ and $R^{19}$, independently of one another, are each hydrogen, $C_1$–$C_6$-alkyl, halogen or a radical of the formula CN, SCN, NCO, OH, $NO_2$, COOH, CHO, $SO_2H$ or $SO_3H$, with the proviso that at least one of the radicals $R^{16}$, $R^{17}$, $R^{18}$ and $R^{19}$ is nitro, and the aromatic ring may additionally be benzofused.

Examples of suitable compounds are 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-methylphenol, 2,4-dinitrochlorobenzene, 2,4-dinitrophenol, 2,4-dinitro-6-sec-butylphenol, 4-cyano-2-nitrophenol and 3-iodo-4-cyano-5-nitrophenol. Aromatic nitro compounds, such as 2,6-dinitro-4-methylphenol, 2-nitro-4-methylphenol, 2,4-dinitro-6-sec-butylphenol or 2,4-dinitro-6-methylphenol, in which one of the radicals $R^{16}$, $R^{17}$, $R^{18}$ and $R^{19}$ is nitro, one is hydroxyl and one is $C_1$–$C_6$-alkyl, are preferably used.

Furthermore, one or more costabilizers selected from the group consisting of the aromatic nitroso compounds, phenothiazines, quinones, hydroquinones and their ethers, phenols and their ethers, hydroxylamines and phenylenediamines may be added to the mixture (B) in addition to the components (i) and (ii).

Examples of suitable aromatic nitroso compounds are p-nitrosophenol, p-nitroso-o-cresol and p-nitroso-N,N'-diethylaniline.

Further costabilizers may also be substituted phenols or hydroquinones, for example the following:

4-tert-butylpyrocatechol, methoxyhydroquinone, 2,6-di-tert-butyl-4-methylphenol, n-octadecyl β-(3,5-di-tert-butyl-4-hydroxyphenyl)-propionate, 1,1,3-tris-(2-methyl-4-hydroxy-5-tert-butyl-phenyl) butane, 1,3,5-trimethyl-2,4,6-tris-(3,5-di-tert-butyl-4-hydroxybenzyl)-benzene, 1,3,5-tris-(3,5-di-tert-butyl-4-hydroxybenzyl) isocyanurate, 1,3,5-tris-[β-(3,5-di-tert-butyl-4-hydroxyphenyl)propionyloxyethyl] isocyanurate, 1,3,5-tris-(2,6-dimethyl-3-hydroxy-4-tert-butylbenzyl) isocyanurate and pentaerythrityl tetrakis-[B-(3,5-di-tert-5 butyl-4-hydroxy-phenyl)-propionate].

For stabilization of the novel monomer compositions, these compositions contain an effective amount of the mixture (B), which in general means from 0.0002 to 5, preferably from 0.0005 to 0.5% by weight, based in each case on the total amount of the monomer composition, of the mixture (B).

The mixtures (B) can of course also contain mixtures of different novel nitroxyl and nitroso compounds and of the stated costabilizers.

Mixture (B) can be added to the monomers before or during the purification or distillation in an effective amount, in order to suppress premature polymerization. In specific cases, it may also be necessary to add the components (i) and (ii), with or without the addition of one or more of the stated costabilizers, separately and then preferably at different points in space.

The novel stabilizer mixtures (B) may be used either as such or as a suspension or solution with the aid of suitable diluents. They can be used generally for inhibiting premature polymerization of, preferably, monomers capable of free radical polymerization and display their stabilizing effect in a broad temperature range. They are effective at any conventional storage temperature from −50 to +50° C. and also at elevated temperature as used, for example in the distillation or purification of the monomers. The pressure range of the stabilization process is also not critical. The stabilizers are effective at atmospheric pressure and also at reduced pressure, as used in some distillation processes.

EXAMPLES

1. Preparation of

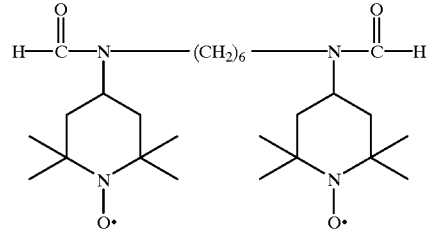

600 ml of a 30% strength by weight aqueous solution of hydrogen peroxide (19.6 mol) were added to a suspension of 540 g (1.37 mol) of N,N'-bis-[2,2,6,6-tetramethylpiperidin-4-yl]-N,N'-bis-formyl-1,6-diaminohexene, 800 ml of water, 150 ml of isobutanol and 200 mg of magnesium sulfate at 70° C. in the course of 2 hours and the mixture was kept at this temperature for a further 16 hours. Thereafter, the mixture was cooled to room temperature and the precipitated product was isolated in the usual manner. Yield: 85%, melting point: from 169 to 170° C.

Characterizations show that the product obtained and used for further experiments (referred to below as F) contains about 60% of the dinitroxyl compound of the above formula.

2. Mixtures:

Steady-state measurements:

500 g of the mixtures stated in Table 1 below and comprising styrene, the product F and the nitro compound 2,4-dinitro-6-sec-butylphenol (DNBP) were heated to 110° C. under nitrogen at atmospheric pressure in a reaction vessel. 250 g per hour of an identical mixture were metered continuously into this thermostated mixture, and the same amount was continuously removed. The equilibrium polymer content was measured in the steady state in the discharge. After 360 minutes, a power failure was simulated (batch operation). The metering of the inhibitor was stopped. The temperature was increased continuously to 145° C. in the course of 60 minutes. The polymer content was measured at intervals of 30 minutes. The following results were obtained.

TABLE 1

| Mixture | Stabilizer (Mixture (B)) | | | | Monomer (A) | | Polymer content in the steady state | Polymer content after batch operation for 60 min |
|---|---|---|---|---|---|---|---|---|
| | Nitroxyl compound | % by weight | Nitro compound | % by weight | vinyl-containing monomer | Stabilizer content of total mixture | | |
| 1 | F | 2 | DNBP | 98 | Styrene | 0.15 | 0.02 | 0.2 |
| 2 | F | 2.9 | DNBP | 97.1 | Styrene | 0.155 | 0.02 | 0.2 |
| 3 | F | 3 | DNBP | 97 | Styrene | 0.10 | 0.04 | 0.6 |
| 4 | F | 1.5 | DNBP | 98.5 | Styrene | 0.20 | — | — |
| Comparison | F | 5 | DNBP | 95 | Styrene | 0.06 | 0.08 | >1 |

Nonsteady-state measurements:

In a 250 ml round-bottomed flask equipped with a stirrer, reflux condenser and an internal thermometer, the mixtures stated in Table 2 were heated to 140° C. under a nitrogen atmosphere by means of an oil bath and were kept at this temperature.

On reaching the final temperature of 140° C., the polymer content was determined at intervals of 15 minutes ($t_o$=0 min is the time when the final temperature was reached).

The results are shown in Table 2.

TABLE 2

| | Change of polymer content as function of time (%) | | | | | | |
|---|---|---|---|---|---|---|---|
| Mixture | 0 min | 15 min | 30 min | 45 min | 60 min | 75 min | 90 min |
| 1 | 0.08 | 0.2 | 0.4 | 0.6 | 1.0 | >2 | — |
| 3 | 0.1 | 0.2 | 0.8 | 1.0 | 2.0 | — | — |
| 4 | 0.06 | 0.1 | 0.2 | 0.4 | 0.8 | 1 | 2 |
| Comparison | 0.2 | 1 | >2 | — | — | — | — |

What is claimed is:

1. A mixture, comprising:
   (A) vinyl-containing monomers; and
   (B) an effective amount of a mixture inhibiting premature polymerization of the vinyl-containing monomers during purification or distillation thereof, and comprising:
   (i) from 0.05 to 4.50% by weight, based on the total mixture (B), of at least one N-oxyl compound of a secondary amine which carries no hydrogen atoms on the α-carbon atoms, and
   (ii) from 99.95 to 99.50% by weight, based on the total mixture (B), of at least one nitro compound.

2. The mixture as claimed in claim 1, containing from 0.1 to 4.0% by weight of component (i), and from 99.9 to 99.6% by weight of component (ii), based in each case on the total mixture (B).

3. The mixture as claimed in claim 1, which contains, as vinyl-containing monomers (A), compounds of the formula (Ia):

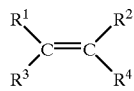

wherein:
$R^1$, $R^2$, $R^3$ and $R^4$ independently of one another, are each hydrogen, $C_1$–$C_6$-alkyl, $C_2$–$C_6$-alkenyl, unsubstituted or substituted aromatic or heteroaromatic radicals or halogen, with the proviso that not more than two or three radicals are simultaneously unsubstituted or substituted aromatic or heteroaromatic radicals.

4. The mixture as claimed in claim 1, which contains, as vinyl-containing monomers (A), compounds of the formula (Ib):

$$CH_2=CH-Q-Z^1 \qquad (Ib)$$

wherein

Q is oxygen or $-NZ^2-$,

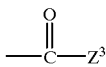

$Z^2$ is hydrogen, or $C_1$–$C_4$-alkyl or, together with $Z^3$, is a saturated or unsaturated $C_3$-, $C_4$- or $C_5$-alkylene bridge in which one or two $CH_2$ groups are optionally replaced by NH, N($C_1$–$C_4$-alkyl), N($C_6$–$C_{10}$-aryl) or oxygen and one or two CH groups are optionally replaced by N and $Z^3$ is hydrogen, $C_1$–$C_4$-alkyl or a radical, which, together with $Z^2$, is a saturated or unsaturated $C_3$-, $C_4$- or $C_5$-alkylene bridge in which one or two $CH_2$ groups are optionally replaced by NH, N($C_1$–$C_4$-alkyl), N($C_6$–$C_{10}$-aryl) or oxygen and one or two CH groups are optionally replaced by N.

5. The mixture as claimed in claim 1, which contains, as component (I), at least one compound of the formula (II):

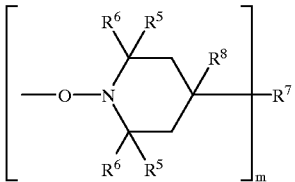

wherein
$R^5$ and $R^6$ independently of one another, are each $C_1$–$C_4$-alkyl or phenyl or, together with the carbon atom to which they are bonded, are a 5- or 6-membered saturated hydrocarbon ring, $R^7$ is hydrogen, hydroxyl, amino or an m-valent organic radical bonded via oxygen or nitrogen or, together with $R^8$, is oxygen or a ring structure as defined for $R^8$, $R^8$ is hydrogen or $C_1$–$C_{12}$-alkyl, or together with $R^7$ is oxygen or, together with $R^7$ and the carbon atom to which they are bonded, forms the following ring structures:

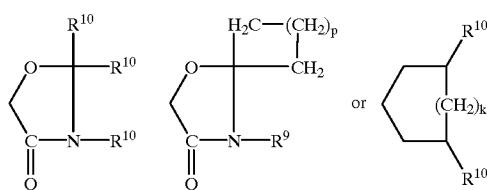
wherein, when $R^7$ together with $R^8$ forms a common radical, m is 1,
$R^9$ is hydrogen, $C_1$–$C_{12}$-alkyl or —(CH$_2$)z—COOR$^{19}$,
$R^{10}$ are identical or different $C_1$–$C_{18}$-alkyl radicals.
k is 0 or 1,
z and p, independently of one another, are each from 1 to 12 and
m is from 1 to 100;
and wherein said m-valent organic radical bonded via oxygen or nitrogen for $R^7$ is selected from the group consisting of
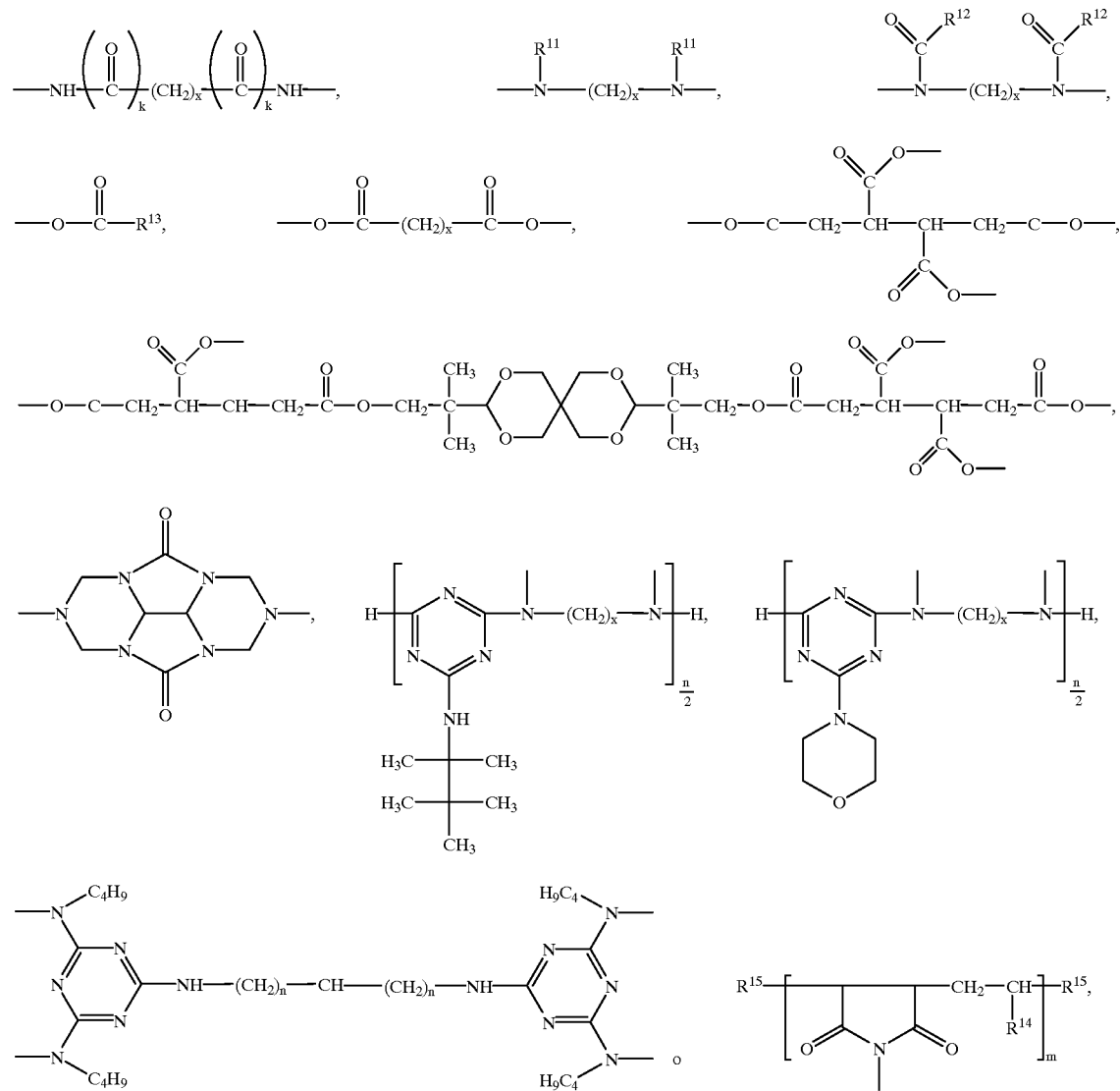

wherein
- $R^{11}$ is $C_1$–$C_{12}$-alkyl or —$(CH_2)_z$—$COOR^{10}$,
- $R^{12}$ is hydrogen or $C_1$–$C_{18}$-alkyl,
- $R^{13}$ us $C_1$–$C_{18}$-alkyl, vinyl or isopropenyl,
- $R^{14}$ is $C_8$–$C_{22}$-alkyl,
- $R^{15}$ is hydrogen or an organic radical as usually formed in the free radical polymerization of the starting monomers (A),
- k is 0 or 1,
- x is from 1 to 12, and
- n is an even number m.

6. The mixture as claimed in claim 1, which contains, as component (ii), at least one aromatic nitro compound of the formula (III)

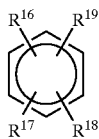
(III)

wherein
- $R^{16}$, $R^{17}$, $R^{18}$ and $R^{19}$ independently of one another, are each hydrogen, $C_1$–$C_6$-alkyl, halogen or a radical of the formula CN, SCN, NCO, OH, $NO_2$, COOH, CHO, $SO_2H$ or $SO_3H$, with the proviso that at least one of the radicals $R^{16}$, $R^{17}$, $R^{18}$ and $R^{19}$ is nitro and the aromatic ring may additionally be benzofused.

7. The mixture as claimed in claim 1, which contains at least one aromatic nitro compound of the formula (III), with the proviso that at least one of the radicals $R^{16}$, $R^{17}$, $R^{18}$ and $R^{19}$ is nitro, one is hydroxyl and one is $C_1$–$C_6$-alkyl.

8. The mixture (B) as claimed in claim 1, which further contains one or more costabilizers selected from the group consisting of the aromatic nitroso compound, phenolthiazines, quinones, hydroquinones and their ethers, phenols and their ethers, hydroxylamines and phenylenediamines, in addition to the components (i) and (ii).

9. A process for inhibiting premature polymerization of monomers as claimed in claim 1, during purification or distillation thereof, which comprises adding an effective amount of the mixture (B) to the monomers before or during the purification or distillation.

10. A process for inhibiting premature polymerization of monomers as claimed in claim 1, during purification or distillation thereof, which comprises adding components of the mixture (B), each individually, in an effective amount, to the monomers before the purification or distillation.

11. The process as claimed in claim 1, wherein the components are added at different steps of the process.

* * * * *

UNITED STATES PATENT AND TRADEMARK OFFICE
CERTIFICATE OF CORRECTION

PATENT NO. : 6,143,205
DATED : November 7, 2000
INVENTOR(S) : Heinz Friedrich SUTORIS et al It is certified that error appears in the above-identified patent and that said Letters Patent is hereby corrected as shown below:

IN THE CLAIMS

Claim 5, for the formula (II), delete

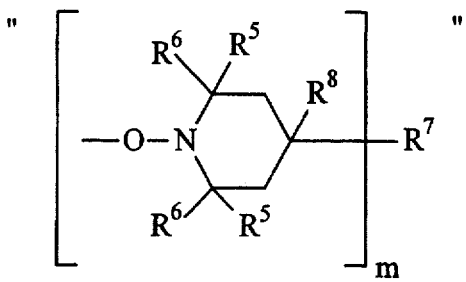

UNITED STATES PATENT AND TRADEMARK OFFICE
CERTIFICATE OF CORRECTION

PATENT NO. : 6,143,205
DATED : Nov. 7, 2000
INVENTOR(S) : Heinz Friedrich Sutoris et al It is certified that error appears in the above-identified patent and that said Letters Patent is hereby corrected as shown below:

and insert therefor:

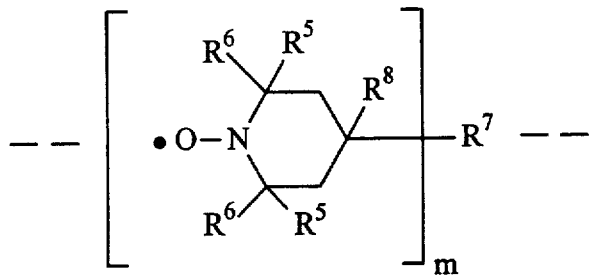

Signed and Sealed this

Twenty-ninth Day of May, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,143,205
APPLICATION NO. : 09/117178
DATED : November 7, 2000
INVENTOR(S) : Heinz Friedrich Sutoris et al.

It is certified that error appears in the above-identified patent and that said Letters Patent is hereby corrected as shown below:

Column 11, line 47 Claim 1, "(ii) from 99.95 to 99.50% by weight based on the total"
should read -- (ii) from 99.95 to 95.50% by weight based on the total --.

Column 11, line 50 Claim 2, "to 4.0% by weight of component (i), and from 99.9 to 99.6%"
should read -- to 4.0% by weight of component (i), and from 99.9 to 96.0% --.

Column 12, line 27 Claim 4, "  "

should read -- $Z^1$ is  or $-Z^3$, --.

Signed and Sealed this

Tenth Day of February, 2009

JOHN DOLL
*Acting Director of the United States Patent and Trademark Office*